(12) United States Patent
Kunicher et al.

(10) Patent No.: US 12,157,002 B1
(45) Date of Patent: Dec. 3, 2024

(54) WEARABLE ELECTRODE DEVICE HAVING MAGNETIC CONNECTORS

(71) Applicant: Neurotrigger Ltd., Tel-Aviv (IL)

(72) Inventors: Nikolai Kunicher, Tel-Aviv (IL); Assaf Deutsch, Tel-Aviv (IL); Michal Marks, Tel-Aviv (IL); Shachar Paz, Tel-Aviv (IL)

(73) Assignee: Neurotrigger Ltd., Tel-Aviv (IL)

( * ) Notice: Subject to any disclaimer, the term of this patent is extended or adjusted under 35 U.S.C. 154(b) by 0 days.

(21) Appl. No.: 18/318,369

(22) Filed: May 16, 2023

(51) Int. Cl.
  *A61N 1/04* (2006.01)
(52) U.S. Cl.
  CPC ......... *A61N 1/0456* (2013.01); *A61N 1/0484* (2013.01)
(58) Field of Classification Search
  CPC .................................................. A61N 1/0456
  USPC ........................................................ 607/48
  See application file for complete search history.

(56) References Cited

U.S. PATENT DOCUMENTS

| | | | |
|---|---|---|---|
| 2015/0360030 A1* | 12/2015 | Cartledge | A61N 1/3603 607/136 |
| 2019/0046787 A1* | 2/2019 | Tyler | A61N 1/0492 |
| 2021/0138232 A1 | 5/2021 | Paz et al. | |

* cited by examiner

*Primary Examiner* — Nicole F Lavert
(74) *Attorney, Agent, or Firm* — Greenberg Traurig, LLP

(57) ABSTRACT

A system includes a wearable device including at least four magnets and a plurality of device electrical connectors, wherein first and second portions of the magnets are positioned to respective first and second sides of a wearable device line of symmetry; and an electrode device including a plurality of magnetic elements and a plurality of electrode electrical connectors, wherein first and second portions of the magnetic elements are positioned to respective first and second sides of an electrode device line of symmetry, wherein a first total magnetic force that is to a first side of the wearable device line of symmetry is sufficiently equal to a second total magnetic force that is to a second wearable device line of symmetry, whereby the first total magnetic force and the second total magnetic force cooperate to retain the device electrical connectors in contact with the electrode electrical connectors.

7 Claims, 10 Drawing Sheets

WEARABLE ELECTRODE DEVICE HAVING MAGNETIC CONNECTORS

FIELD OF THE INVENTION

The present disclosure is related to devices for transcutaneous nerve stimulation such as facial nerve stimulation, and in particular, but not exclusive, to using non-invasive nerve stimulation for artificially eliciting eye blink, such as with humans with acute facial paralysis. The present disclosure is also related to magnetic interconnections between reusable wearable devices and consumable electrode contacts.

BACKGROUND OF THE INVENTION

Facial nerve paralysis can result from a variety of underlying conditions. Patients suffering from facial nerve paralysis may have difficulty blinking, which may result in complications such as dry eyes.

SUMMARY OF THE DISCLOSURE

In some embodiments, a system includes a wearable device configured to artificially stimulate a facial nerve or muscle and an electrode device, the wearable device including: a pulse generator configured to generate a signal; and a wearable device connector portion, wherein the wearable device connector portion includes: a first wearable device electrical connector and a second wearable device electrical connector, wherein the first wearable device electrical connector and the second wearable device electrical connector are electrically coupled to the pulse generator, wherein the first wearable device electrical connector and the second wearable device electrical connector define a wearable device connector axis that extends through a center of the first wearable device electrical connector and a center of the second wearable device electrical connector, and at least four magnets, wherein a first at least one of the magnets is positioned to a first side of the wearable device connector axis, wherein a second at least one of the magnets is positioned to a second side of the wearable device connector axis that is opposite the first side of the wearable device connector axis, and wherein the at least four magnets define a wearable device line of symmetry, wherein a first portion of the first at least one of the magnets is positioned to a first side of the wearable device line of symmetry, wherein a second portion of the first at least one of the magnets is positioned to a second side of the wearable device line of symmetry that is opposite the first side of the wearable device line of symmetry, wherein a first portion of the second at least one of the magnets is positioned to the first side of the wearable device line of symmetry, and wherein a second portion of the second at least one of the magnets is positioned to the second side of the wearable device line of symmetry; and wherein the electrode device includes: at least two electrodes configured to be attachable to human body scalp at temporal skin of the human body scalp; and an electrode connector portion, wherein the electrode connector portion includes: a first electrode electrical connector electrically coupled to a first one of the two electrodes and a second electrode electrical connector electrically coupled to a second one of the two electrodes, wherein the first electrode electrical connector and the second electrode electrical connector define an electrode connector axis that extends through a center of the first electrode electrical connector and a center of the second electrode electrical connector, and a plurality of magnetic elements, wherein a first at least one of the magnetic elements is positioned to a first side of the electrode connector axis, wherein a second at least one of the magnetic elements is positioned to a second side of the electrode connector axis that is opposite the first side of the electrode connector axis, wherein the plurality of magnetic elements define an electrode device line of symmetry, wherein a first portion of the first at least one of the magnetic elements is positioned to a first side of the electrode device line of symmetry, wherein a second portion of the first at least one of the magnetic elements is positioned to a second side of the electrode line of symmetry that is opposite the first side of the electrode device line of symmetry, wherein a first portion of the second at least one of the magnetic elements is positioned to the first side of the electrode device line of symmetry, and wherein a second portion of the second at least one of the magnetic elements is positioned to the second side of the electrode device line of symmetry; wherein the plurality of magnets and the plurality of magnetic elements are configured such that, when the electrode device is positioned adjacent to the wearable device such that (a) the first device electrical connector contacts the first electrode electrical connector, (b) the second device electrical connector contacts the second electrode electrical connector, (c) the wearable device connector axis is aligned with the electrode device connector axis, and (d) the wearable device line of symmetry is aligned with the electrode device line of symmetry, a first total magnetic force that is a sum of (1) a magnetic attractive force between the first portion of the first at least one of the magnets and the first portion of the first at least one of the magnetic elements and (2) a magnetic attractive force between the first portion of the second at least one of the magnets and the first portion of the second at least one of the magnetic elements is sufficiently equivalent to a second total magnetic force that is a sum of (1) a magnetic attractive force between the second portion of the first at least one of the magnets and the second portion of the first at least one of the magnetic elements and (2) a magnetic attractive force between the second portion of the second at least one of the magnets and the second portion of the second at least one of the magnetic elements, whereby the first total magnetic force and the second total magnetic force cooperate to retain the first device electrical connector in contact with the first electrode electrical connector and to retain the second device electrical connector in contact with the second electrode electrical connector, thereby to allow the signal generated by the pulse generator to be conveyed to the two electrodes.

In some embodiments, the plurality of magnetic elements are magnets.

In some embodiments, the plurality of magnetic elements include a ferromagnetic metal.

In some embodiments, the at least four magnets includes eight magnets. In some embodiments, four of the magnets are positioned to the first side of the wearable device connector axis and four of the magnets are positioned to the second side of the wearable device connector axis.

In some embodiments, the wearable device line of symmetry is perpendicular to the wearable device connector axis. In some embodiments, the wearable device line of symmetry is equidistant from the center of the first wearable device electric connector and from the center of the second wearable device electric connector.

In some embodiments, a quantity of the magnetic elements is equal to a quantity of the at least four magnets.

In some embodiments, the electrode device line of symmetry is perpendicular to the electrode device connector axis. In some embodiments, the wearable device line of symmetry is equidistant from the center of the first electrode device electric connector and from the center of the second electrode device electric connector.

In some embodiments, the first total magnetic force that is sufficiently equivalent to the second total magnetic force is within plus or minus 20% of the second total magnetic force. In some embodiments, the first total magnetic force that is sufficiently equivalent to the second total magnetic force is within plus or minus 10% of the second total magnetic force.

In some embodiments, an electrode component is configured to magnetically connect to a wearable device configured to artificially stimulate a facial nerve or muscle, wherein the wearable device includes: a pulse generator configured to generate a signal; and a wearable device connector portion, wherein the wearable device connector portion includes: a first wearable device electrical connector and a second wearable device electrical connector, wherein the first wearable device electrical connector and the second wearable device electrical connector are electrically coupled to the pulse generator, wherein the first wearable device electrical connector and the second wearable device electrical connector define a wearable device connector axis that extends through a center of the first wearable device electrical connector and a center of the second wearable device electrical connector, and at least four magnets, wherein a first at least one of the magnets is positioned to a first side of the wearable device connector axis, wherein a second at least one of the magnets is positioned to a second side of the wearable device connector axis that is opposite the first side of the wearable device connector axis, and wherein the at least four magnets define a wearable device line of symmetry, wherein a first portion of the first at least one of the magnets is positioned to a first side of the wearable device line of symmetry, wherein a second portion of the first at least one of the magnets is positioned to a second side of the wearable device line of symmetry that is opposite the first side of the wearable device line of symmetry, wherein a first portion of the second at least one of the magnets is positioned to the first side of the wearable device line of symmetry, and wherein a second portion of the second at least one of the magnets is positioned to the second side of the wearable device line of symmetry; wherein the electrode component includes: two electrodes configured to be attachable to human body scalp at temporal skin of the human body scalp; an electrode connector portion, wherein the electrode connector portion includes: a first electrode electrical connector electrically coupled to a first one of the two electrodes and a second electrode electrical connector electrically coupled to a second one of the two electrodes, wherein the first electrode electrical connector and the second electrode electrical connector define an electrode connector axis that extends through a center of the first electrode electrical connector and a center of the second electrode electrical connector, and a plurality of magnetic elements, wherein a first at least one of the magnetic elements is positioned to a first side of the electrode connector axis, wherein a second at least one of the magnetic elements is positioned to a second side of the electrode connector axis that is opposite the first side of the electrode connector axis, wherein the plurality of magnetic elements define an electrode device line of symmetry, wherein a first portion of the first at least one of the magnetic elements is positioned to a first side of the electrode device line of symmetry, wherein a second portion of the first at least one of the magnetic elements is positioned to a second side of the electrode line of symmetry that is opposite the first side of the electrode device line of symmetry, wherein a first portion of the second at least one of the magnetic elements is positioned to the first side of the electrode device line of symmetry, and wherein a second portion of the second at least one of the magnetic elements is positioned to the second side of the electrode device line of symmetry; wherein the plurality of magnetic elements are configured such that, when the electrode device is positioned adjacent to the wearable device such that (a) the first device electrical connector contacts the first electrode electrical connector, (b) the second device electrical connector contacts the second electrode electrical connector, (c) the wearable device connector axis is aligned with the electrode device connector axis, and (d) the wearable device line of symmetry is aligned with the electrode device line of symmetry, a first total magnetic force that is a sum of (1) a magnetic attractive force between the first portion of the first at least one of the magnets and the first portion of the first at least one of the magnetic elements and (2) a magnetic attractive force between the first portion of the second at least one of the magnets and the first portion of the second at least one of the magnetic elements is sufficiently equivalent to a second total magnetic force that is a sum of (1) a magnetic attractive force between the second portion of the first at least one of the magnets and the second portion of the first at least one of the magnetic elements and (2) a magnetic attractive force between the second portion of the second at least one of the magnets and the second portion of the second at least one of the magnetic elements, whereby the first total magnetic force and the second total magnetic force cooperate to retain the first device electrical connector in contact with the first electrode electrical connector and to retain the second device electrical connector in contact with the second electrode electrical connector, thereby to allow the signal generated by the pulse generator to be conveyed to the two electrodes.

In some embodiments, the first total magnetic force that is sufficiently equivalent to the second total magnetic force is within plus or minus 20% of the second total magnetic force.

In some embodiments, the plurality of magnetic elements include a ferromagnetic metal.

In some embodiments, the wearable device line of symmetry is perpendicular to the wearable device connector axis. In some embodiments, the wearable device line of symmetry is equidistant from the center of the first wearable device electric connector and from the center of the second wearable device electric connector.

In some embodiments, a quantity of the magnetic elements is equal to a quantity of the at least four magnets.

In some embodiments, the electrode device line of symmetry is perpendicular to the electrode device connector axis. In some embodiments, the wearable device line of symmetry is equidistant from the center of the first electrode device electric connector and from the center of the second electrode device electric connector.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION OF THE DRAWINGS

Figure 1:
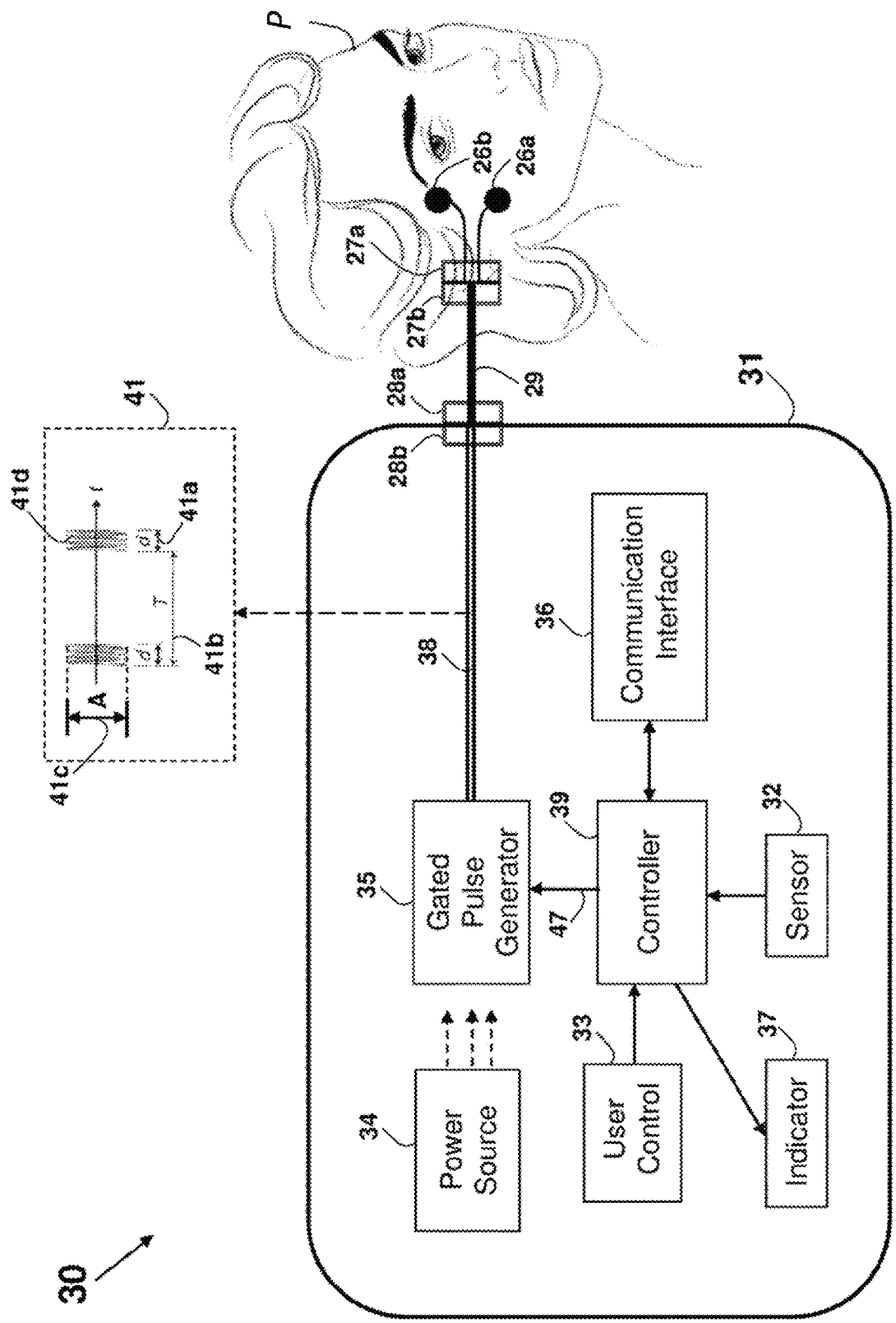
FIG. 1 shows an exemplary embodiment of a system.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

The exemplary embodiments relate to stimulating devices configured to generate modulated pulse bursts and to deliver such bursts to a nerve, such as a facial nerve, via a coupling device. In some embodiments, device output is controlled manually or automatically. In some embodiments, device output is synchronized with an opposite eye or by a preset program. In some embodiments, an exemplary device is configured to generate timed eye blinking by inducing muscle action to close one or both eyelids, either independently or in combination, to result in complete eye closure. In some embodiments, an exemplary device is configured to stimulate or squeeze the tear gland.

FIG. 1 shows an exemplary embodiment of a system 30 using a stimulator device 31 (e.g., a wearable device). In some embodiments, the device 31 includes a generator 35 (e.g., a gated pulse generator) that outputs, via a connection or port 38, a pulse signal 41 (e.g., a gated symmetrical or asymmetrical bi-phasic square pulse signal). In some embodiments, the signal 41 includes a sequence of square wave bursts 41d having a peak-to-peak amplitude 'A' 41c and a time duration "d" 41a. In some embodiments, the pulse sequence 41d is periodically repeated every "T" 41b seconds, and in each burst 41d the square-wave frequency is 'f'. In some embodiments, the signal 41 output by the generator 35 output signal 41 is carried over a connection 38 to a wearable device connector portion 28b in an enclosure of the device 31.

In some embodiments, the system 30 includes an electrode device 27. In some embodiments, the electrode device 27 includes electrodes 26a and 26b that are electrically coupled (e.g., by wires, conductors, etc.) to an electrode connector portion 27a. In some embodiments, the electrodes 26a and 26b are configured to be removably attached to temporal skin of a human body scalp of a person P. In some embodiments, the system 30 includes a cable 29 connecting the electrode device 27 to the stimulator device 31. In some embodiments, as will be described hereinafter, no cable 29 is present, and the electrode device 27 is directly coupled to the stimulator device 31 (e.g., the electrode connector portion 27a and the wearable device connector portion 28b are configured to be coupled directly to one another). In some embodiments, the cable 29 includes a first end 29a coupled to the wearable device connector portion 28b and a second end 29b coupled to the electrode connector portion 27a. In some embodiments, the stimulator device 31, the cable 29, and the electrode device 27 form a continuous electrical path from the generator 35 to the skin of the treated person P. In some embodiments, when the system 30 is in use, the signal 41 is thereby conveyed from the generator 35 to the electrodes 26a and 26b to thereby treat the person P.

In some embodiments, operation of the device 31 is controlled by a controller block 39. In some embodiments, the controller block 39 includes a software (or firmware) and a processor for executing the software (or firmware). In some embodiments, the controller 39 controls and set the parameters of the signal 41, such as the burst duration 'd' 41a, the repetition period 'T' 41b, the amplitude "A" 41c, the burst internal frequency 41d, or any combination thereof, via a connection 47 between the controller 39 and the generator 35. In some embodiments, the device 31 comprises a 32 that captures and outputs sensor data in response to a physical phenomenon. In some embodiments, the sensor 32 is coupled to the controller 39 to thereby data captured by the sensor 32 to the controller 39 for further handling and processing (e.g., for the controller 39 to control the signal 41 in response to the data captured by the sensor 32).

In some embodiments, the device 31 includes an indicator 37 that is an output component for notifying or outputting information to a user, which may be the person P that is treated by the system 30 or may be another person. For example, in some embodiments the indicator 37 provides auditory and/or visual feedback to a user, such as to alert the user through auditory tones/beeps in advance of the presentation of information, or by changes in a display. In some embodiments, the indicator 37 includes a haptic element to provide tactile feedback to the user, such as the person P wearing the device 31. In some embodiments, the indicator 37 is coupled to be controlled or activated by the controller 39.

In some embodiments, the device 31 includes a user control functionality 33 that is an input component for receiving information or control commands from a user, which may be the person P that is treated by the system 30, or may be another person. In some embodiments, the user control functionality 33 includes an input component, e.g., a piece of computer hardware equipment used to provide data and control signals to an information processing system such as a computer or information appliance. In some embodiments, such an input component is an integrated or a peripheral input device (e.g., hard/soft keyboard, mouse, resistive or capacitive touch display, etc.). Examples of input components include keyboards, mice, scanners, digital cameras and joysticks.

In some embodiments, the device 31 includes a communication interface 36 for transmitting data to, or for receiving data from, another device over a communication network. In some embodiments, the communication interface 36 consists of, is part of, or includes a transceiver or modem for communication with the network. In some embodiments, in the case of wired networks, the communication interface 36 connects to the network via a port that may include a connector. In some embodiments, in the case of wireless networks, the communication interface 36 connects to the network via a port that may include an antenna. In some embodiments, the communication interface 36 is controlled and activated by the controller 39. In some embodiments, data received from an external device over the communication network via the communication interface 36 is transferred to the controller 39 for further handling (e.g., for the controller 39 to control the signal 41), and data to be sent to an external device over the communication network is received at the communication interface 36 from the controller 39.

In some embodiments, the controller 39 is based on a discrete logic or an integrated device, such as a processor, microprocessor or microcomputer, and may include a general-purpose device or may be a special purpose processing device, such as an ASIC, PAL, PLA, PLD, Field Programmable Gate Array (FPGA), Gate Array, or other customized or programmable device. In the case of a programmable device as well as in other implementations, a memory is required. In some embodiments, the controller 39 includes a memory that may include a static RAM (random Access Memory), dynamic RAM, flash memory, ROM (Read Only Memory), or any other data storage medium. In some embodiments, the memory includes data, programs, and/or instructions and any other software or firmware executable by the processor. In some embodiments, control logic is implemented in hardware or in software, such as a firmware stored in the memory. In some embodiments, the controller 39 controls and monitors operation of the device 31, such as initialization, configuration, interface, and commands. In some embodiments, any step, method, or flowchart described herein may be performed by the processor in the controller 39 as directed by the software therein.

In some embodiments, electronic circuits and components in the stimulating device 31 are electrically powered from a power source 34. In some embodiments, the power source 34 supplies a direct current. In some embodiments, the power source 34 is, includes, or is based on a battery. In some embodiments, a battery is a disposable battery or a rechargeable battery.

In some embodiments, the gated pulse generator 35 is a signal generator that serves as a current (or voltage) source for providing the burst sequence 41 to the wearable device connector 28b of the device 31, for supplying via the cable 29 to the person P. In some embodiments, activation of the generator 35, as well as the controlling and setting of parameters of the burst sequence 41, is performed by the controller 39. In some embodiments, the gated pulse generator 35 supplies asymmetrical bi-phasic square current pulses.

In some embodiments, parameters of the burst sequence 41 include the a peak-to-peak amplitude 'A' 41c (e.g., the nominal value, or effective value, of the burst sequence 41), the burst duration d 41a, the frequency 'f' of the signal in the burst 41d, and the period T 41b. In some embodiments, each of the parameters is implemented as fixed value, and as such cannot be changed during operation of the device 31. In some embodiments, one, some, or all of the parameters can be changed or controlled before or during operation of the device 31, such as by the user using the user control 33, externally using a connected device in communication with the device 31 via the communication interface 36, or in response to output of the sensor 32. In some embodiments, each such changeable parameter may be variable over a range from a minimum value to a maximum value, as set by the controller 39 over the control connection or the port 47.

In some embodiments, the gated pulse generator 35 is a voltage generator. In some embodiments, the gated pulse generator 35 is a current generator. In some embodiments, the peak-to-peak amplitude 'A' 41c, the nominal value, or effective value, of the signal 41, in case of a current generator, (or the minimum or maximum settable value) may be above 0.1 milliampere (mA), 0.2 mA, 0.5 mA, 0.8 mA, 1 mA, 1.2 mA, 1.5 mA, 1.8 mA, 2 mA, 2.5 mA, 3 mA, 3.5 mA, 4 mA, 4.5 mA, 5 mA, 5.5 mA, 6 mA, 7 mA, 8 mA, 9 mA, 10 mA, 11 ma, 12 mA, 15 mA, 18 mA, 20 mA, 22 mA, 25 mA, 30 mA, 35 mA, 40 mA, 45 mA, 50 mA, 55 mA, 60 mA, 65 mA, 70 mA, 75 mA, 80 mA, or 100 mA. In some embodiments, the peak-to-peak amplitude 'A' 41c, or the nominal or effective value, of the signal 41, in case of a current generator, (or the minimum or maximum settable value) may be below 0.2 milliampere (mA), 0.5 mA, 0.8 mA, 1 mA, 1.2 mA, 1.5 mA, 1.8 mA, 2 mA, 2.5 mA, 3 mA, 3.5 mA, 4 mA, 4.5 mA, 5 mA, 5.5 mA, 6 mA, 7 mA, 8 mA, 9 mA, 10 mA, 11 ma, 12 mA, 15 mA, 18 mA, 20 mA, 22 mA, 25 mA, 30 mA, 35 mA, 40 mA, 45 mA, 50 mA, 55 mA, 60 mA, 65 mA, 70 mA, 75 mA, 80 mA, 100 mA, or 150 mA.

In some embodiments, in case of a voltage generator, the peak-to-peak amplitude 'A' 41c, the nominal value, or the effective value, of the signal 41, in case of a current generator, (or the minimum or maximum settable value) may be above 0.1 millivolt (mV), 0.2 mV, 0.5 mV, 0.8 mV, 1 mV, 1.2 mV, 1.5 mV, 1.8 mV, 2 mV, 2.5 mV, 3 mV, 3.5 mV, 4 mV, 4.5 mV, 5 mV, 5.5 mV, 6 mV, 7 mV, 8 mV, 9 mV, 10 mV, 11 mV, 12 mV, 15 mV, 18 mV, 20 mV, 22 mV, 25 mV, 30 mV, 35 mV, 40 mV, 45 mV, 50 mV, 55 mV, 60 mV, 65 mV, 70 mV, 75 mV, 80 mV, or 100 mV. In some embodiments, in case of a voltage generator, the peak-to-peak amplitude 'A' 41c, the nominal value, or the effective value, of the signal 41, (or the minimum or maximum settable value) may be below 0.2 millivolt (mV), 0.5 mV, 0.8 mV, 1 mV, 1.2 mV, 1.5 mV, 1.8 mV, 2 mV, 2.5 mV, 3 mV, 3.5 mV, 4 mV, 4.5 mV, 5 mV, 5.5 mV, 6 mV, 7 mV, 8 mV, 9 mV, 10 mV, 11 mV, 12 mV, 15 mV, 18 mV, 20 mV, 22 mV, 25 mV, 30 mV, 35 mV, 40 mV, 45 mV, 50 mV, 55 mV, 60 mV, 65 mV, 70 mV, 75 mV, 80 mV, 100 mV, or 150 mV. In some embodiments, in case of a voltage generator, the peak-to-peak amplitude 'A' 41c, the nominal value, or the effective value, of the signal 41, in case of a current generator, (or the minimum or maximum settable value) may be above 0.1 Volts (V), 0.2 V, 0.5 V, 0.8 V, 1 V, 1.2 V, 1.5 V, 1.8 V, 2 V, 2.5 V, 3 V, 3.5 V, 4 V, 4.5 V, 5 V, 5.5 V, 6 V, 7 V, 8 V, 9 V, 10 V, 11 V, 12 V, 15 V, 18 V, 20 V, 22 V, 25 V, 30 V, 35 V, 40 V, 45 V, 50 V, 55 V, 60 V, 65 V, 70 V, 75 V, 80 V, or 100 V. In some embodiments, in case of a voltage generator, the peak-to-peak amplitude 'A' 41c, the nominal value, or the effective value, of the signal 41, (or the minimum or maximum settable value) may be below 0.2 Volts (V), 0.5 V, 0.8 V, 1 V, 1.2 V, 1.5 V, 1.8 V, 2 V, 2.5 V, 3 V, 3.5 V, 4 V, 4.5 V, 5 V, 5.5 V, 6 V, 7 V, 8 V, 9 V, 10 V, 11 V, 12 V, 15 V, 18 V, 20 V, 22 V, 25 V, 30 V, 35 V, 40 V, 45 V, 50 V, 55 V, 60 V, 65 V, 70 V, 75 V, 80 V, 100 V, or 150 V.

In some embodiments, the burst duration d 41a of the gated pulse generator 35 output (or the minimum or maximum settable value) may be above 1 milliseconds (ms), 2 ms, 3 ms, 5 ms, 7 ms, 10 ms, 12 ms, 15 ms, 18 ms, 20 ms, 25 ms, 30 ms, 40 ms, 45 ms, 50 ms, 100 ms, 120 ms, 150 ms, 180 ms, 200 ms, 250 ms, 300 ms, 400 ms, 450 ms, or 500 ms. In some embodiments, the burst duration d 41a (or the minimum or maximum settable value) may be below 2 milliseconds (ms), 2 ms, 3 ms, 5 ms, 7 ms, 10 ms, 12 ms, 15 ms, 18 ms, 20 ms, 25 ms, 30 ms, 40 ms, 45 ms, 50 ms, 100 ms, 120 ms, 150 ms, 180 ms, 200 ms, 250 ms, 300 ms, 400 ms, 450 ms, 500 ms, or 900 ms.

In some embodiments, the frequency 'f' of the signal in the burst 41d (or the minimum or maximum settable value) may be above 1 Hertz (Hz), 2 Hz, 5 Hz, 8 Hz, 10 Hz, 12 Hz, 15 Hz, 18 Hz, 20 Hz, 22 Hz, 25 Hz, 30 Hz, 35 Hz, 50 Hz, 60 Hz, 70 Hz, 80 Hz, 100 Hz, 120 Hz, 150 Hz, 180 Hz, 200 Hz, 250 Hz, 300 Hz, 350 Hz, 400 Hz, or 500 Hz. In some embodiments, the frequency 'f' of the signal in the burst 41d (or the minimum or maximum settable value) may be below 2 Hertz (Hz), 5 Hz, 8 Hz, 10 Hz, 12 Hz, 15 Hz, 18 Hz, 20 Hz, 22 Hz, 25 Hz, 30 Hz, 35 Hz, 50 Hz, 60 Hz, 70 Hz, 80 Hz, 100 Hz, 120 Hz, 150 Hz, 180 Hz, 200 Hz, 250 Hz, 300 Hz, 350 Hz, 400 Hz, 500 Hz, or 1,000 Hz.

In some embodiments, the period T 41b of the signal between consecutive ones of the bursts 41d (or the minimum or maximum settable value) may be above 100 milliseconds (ms), 120 ms, 150 ms, 180 ms, 200 ms, 250 ms, 300 ms, 400 ms, 450 ms, 500 ms, 700 ms, 1,000 ms, 1,200 ms, 1,500 ms, 1,800 ms, 2,000 ms, 2,500 ms, 3,000 ms, 3,500 ms, 4,000 ms, 4,500 ms, 5,000 ms, 6,000 ms, 6,500 ms, 7,000 ms, 7,500 ms, 8000 ms, 8500 ms, 9000 ms, or 9500 ms. In some embodiments, the period T 41b of the signal between consecutive ones of the bursts 41d (or the minimum or maximum settable value) may be below 120 ms, 150 ms, 180 ms, 200 ms, 250 ms, 300 ms, 400 ms, 450 ms, 500 ms, 700 ms, 1,000 (ms), 1,200 ms, 1,500 ms, 1,800 ms, 2,000 ms, 2,500 ms, 3,000 ms, 3,500 ms, 4,000 ms, 4,500 ms, 5,000 ms, 6,000 ms, 6,500 ms, 7,000 ms, 7,500 ms, 8,000 ms, 8,500 ms, 9,000 ms, 9,500 ms, or 10,000 ms.

Figure 2:
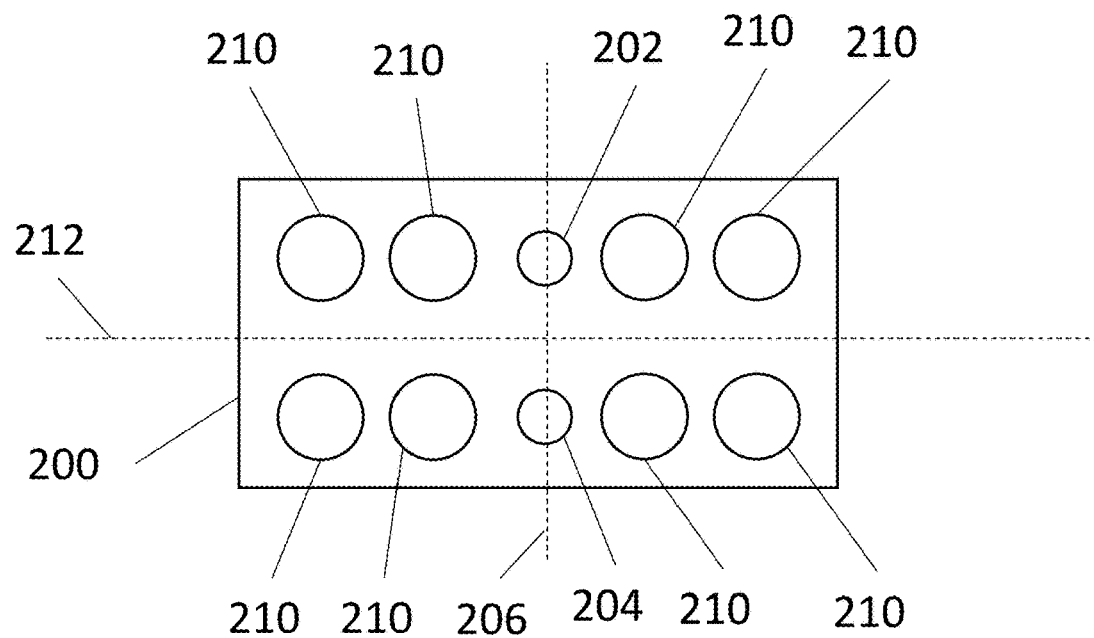
FIG. 2 shows an exemplary embodiment of a connector portion of a wearable device.

In some embodiments, a wearable device (e.g., a wearable stimulator device) and an electrode device are configured to be removably coupled to one another magnetically. FIG. 2 illustrates an exemplary wearable device connector portion 200 (e.g., performing a function similar to that of the wearable device connector portion 28b described above) configured for use in such an embodiment of the wearable device 31. In some embodiments, the wearable device connector portion 200 includes a first wearable device electrical connector 202 and a second wearable device electrical connector 204. In some embodiments, the first wearable device electrical connector 202 and the second wearable device electrical connector are pins, such as the type of spring-loaded pins typically referred to as pogo pins. In other embodiments, the wearable device connector portion 200 may include a different quantity of electrical connectors (e.g., one, three, four, five, six, etc.). In some embodiments, the first wearable device electrical connector 202 and the second wearable device electrical connector 204 define a wearable device connector axis 206 extending through the respective centers thereof.

In some embodiments, the wearable device connector portion 200 includes a plurality of magnets 210, e.g., at least two of the magnets 210, or at least four of the magnets 210, or at least eight of the magnets 210. In some embodiments, at least one of the plurality of magnets 210 is located to a first side of the wearable device connector axis 206 (e.g., to the left side as shown in FIG. 2) and at least one of the plurality of magnets 210 is located to a second side of the wearable device connector axis 206 (e.g., to the right side as shown in FIG. 2). In the embodiment shown in FIG. 2, the wearable device connector portion 200 includes eight of the magnets 210, four of which are located to a first side of the wearable device connector axis 206 (e.g., to the left side as shown in FIG. 2) and four of which are located to a second side of the wearable device connector axis 206 (e.g., to the right side as shown in FIG. 2).

In some embodiments, the plurality of magnets 210 define a wearable device line of symmetry 212. In some embodiments, the wearable device line of symmetry 212 is perpendicular to the wearable device connector axis 206. In some embodiments, the wearable device line of symmetry 212 intersects the wearable device connector axis 206 at a location midway between the first wearable device electrical connector 202 and the second wearable device electrical connector 204. As discussed above, in some embodiments, at least one of the plurality of magnets 210 is located to a first side of the wearable device connector axis 206 (e.g., to the left side as shown in FIG. 2). In some embodiments, at least a portion of the at least one of the plurality of magnets 210 that is located to the first side of the wearable device connector axis 206 is also located to a first side of the wearable device line of symmetry 212 (e.g., above the wearable device line of symmetry 212 as shown in FIG. 2), and at least a portion of the at least one of the plurality of magnets 210 that is located to the first side of the wearable device connector axis 206 is also located to a second side of the wearable device line of symmetry 212 (e.g., below the wearable device line of symmetry 212 as shown in FIG. 2). For example, in the embodiment shown in FIG. 2, two of the magnets 210 are located to a first side of the wearable device connector axis 206 (e.g., to the left side as shown in FIG. 2) and to a first side of the wearable device line of symmetry 212 (e.g., above the wearable device line of symmetry 212 as shown in FIG. 2), and two of the magnets 210 are located to the first side of the wearable device connector axis 206 (e.g., to the left side as shown in FIG. 2) and to a second side of the wearable device line of symmetry 212 (e.g., below the wearable device line of symmetry 212 as shown in FIG. 2). Similarly, in some embodiments, at least a portion of the at least one of the plurality of magnets 210 that is located to the second side of the wearable device connector axis 206 is also located to a first side of the wearable device line of symmetry 212 (e.g., above the wearable device line of symmetry 212 as shown in FIG. 2), and at least a portion of the at least one of the plurality of magnets 210 that is located to the second side of the wearable device connector axis 206 is also located to a second side of the wearable device line of symmetry 212 (e.g., below the wearable device line of symmetry 212 as shown in FIG. 2). For example, in the embodiment shown in FIG. 2, two of the magnets 210 are located to a second side of the wearable device connector axis 206 (e.g., to the right side as shown in FIG. 2) and to a first side of the wearable device line of symmetry 212 (e.g., above the wearable device line of symmetry 212 as shown in FIG. 2), and two of the magnets 210 are located to the second side of the wearable device connector axis 206 (e.g., to the left side as shown in FIG. 2) and to a second side of the wearable device line of symmetry 212 (e.g., below the wearable device line of symmetry 212 as shown in FIG. 2). In some embodiments, the arrangement of the magnets 210 facilitates engagement of the wearable device connector portion 200 to an electrode device connector portion as will be described hereinafter.

Figure 3:
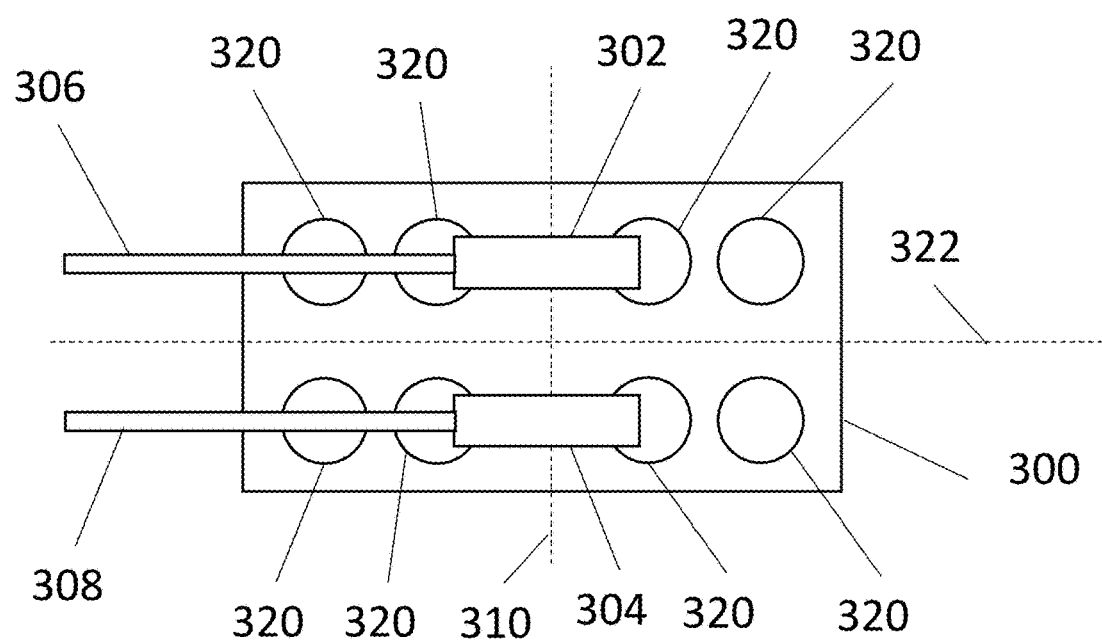
FIG. 3 shows an exemplary embodiment of a connector portion of an electrode device.

FIG. 3 illustrates an exemplary electrode device connector portion 300 (e.g., performing a function similar to that of the electrode connector portion 27a described above) configured for use together with the exemplary wearable device connector portion 200 in an embodiment of the wearable device 31 in which the wearable device and the electrode device are coupled to one another magnetically. In some embodiments, the electrode device connector portion 300 includes a first electrode electrical connector 302 and a second electrode electrical connector 304. In some embodiments, the first electrode electrical connector 302 and the second electrode electrical connector 304 are contact pads. In some embodiments, the first electrode electrical connector 302 and the second electrode electrical connector 304 are electrically connected to respective first and second conductors 306 and 308, which in turn are electrically connected to respective first and second electrodes.

In some embodiments, the first electrode electrical connector 302 and the second electrode electrical connector 304 define an electrode connector axis 310. In some embodiments, the electrode connector axis 310 extends through the respective centers of the first electrode electrical connector 302 and the second electrode electrical connector 304.

In some embodiments, the electrode device connector portion 300 includes a plurality of magnetic elements 320. In some embodiments, the plurality of magnetic elements 320 includes at least two of the magnetic elements 320, or at least four of the magnetic elements 320, or at least eight of the magnetic elements 320. In some embodiments, a quantity of the plurality of magnetic elements 320 is the same as a quantity of the plurality of magnets 210. In some embodiments, a quantity of the plurality of magnetic elements 320 different from a quantity of the plurality of magnets 210. In some embodiments, the magnetic elements 320 include magnets. In some embodiments, the magnetic elements 320 do not include magnets. In some embodiments, the magnetic elements 320 include a magnetic material (e.g., a magnetic metal, such as a ferrous metal) and do not include magnets.

In some embodiments, at least one of the plurality of magnetic elements 320 is located to a first side of the electrode connector axis 310 (e.g., to the left side as shown in FIG. 3) and at least one of the plurality of magnetic elements 320 is located to a second side of the electrode connector axis 310 (e.g., to the right side as shown in FIG. 3). In the embodiment shown in FIG. 3, the electrode device connector portion 300 includes eight of the magnetic elements 320, four of which are located to a first side of the electrode connector axis 310 (e.g., to the left side as shown in FIG. 3) and four of which are located to a second side of the electrode connector axis 310 (e.g., to the right side as shown in FIG. 3).

In some embodiments, the plurality of magnetic elements 320 define an electrode device line of symmetry 322. In some embodiments, the electrode device line of symmetry 322 is perpendicular to the electrode connector axis 310. In some embodiments, the electrode device line of symmetry 322 intersects the electrode connector axis 310 at a location midway between the first electrode electrical connector 302 and the second electrode electrical connector 304. As discussed above, in some embodiments, at least one of the plurality of magnetic elements 320 is located to a first side of the electrode connector axis 310 (e.g., to the left side as shown in FIG. 3). In some embodiments, at least a portion of the at least one of the plurality of magnetic elements 320 that is located to the first side of the electrode connector axis 310 is also located to a first side of the electrode device line of symmetry 322 (e.g., above the electrode device line of symmetry 322 as shown in FIG. 3), and at least a portion of the at least one of the plurality of magnetic elements 320 that is located to the first side of the electrode connector axis 310 is also located to a second side of the electrode device line of symmetry 322 (e.g., below the electrode device line of symmetry 322 as shown in FIG. 3). For example, in the embodiment shown in FIG. 3, two of the magnetic elements 320 are located to a first side of the electrode connector axis 310 (e.g., to the left side as shown in FIG. 3) and to a first side of the electrode device line of symmetry 322 (e.g., above the electrode device line of symmetry 322 as shown in FIG. 3), and two of the magnetic elements 320 are located to the first side of the electrode connector axis 310 (e.g., to the left side as shown in FIG. 3) and to a second side of the electrode device line of symmetry 322 (e.g., below the electrode device line of symmetry 322 as shown in FIG. 3). Similarly, in some embodiments, at least a portion of the at least one of the plurality of magnetic elements 320 that are located to the second side of the electrode connector axis 310 is also located to a first side of the electrode device line of symmetry 322 (e.g., above the electrode device line of symmetry 322 as shown in FIG. 3), and at least a portion of the at least one of the plurality of magnetic elements 320 that is located to the second side of the electrode connector axis 310 is also located to a second side of the electrode device line of symmetry 322 (e.g., below the electrode device line of symmetry 322 as shown in FIG. 3). For example, in the embodiment shown in FIG. 3, two of the magnetic elements 320 are located to a second side of the electrode connector axis 310 (e.g., to the right side as shown in FIG. 3) and to a first side of the electrode device line of symmetry 322 (e.g., above the electrode device line of symmetry 322 as shown in FIG. 3), and two of the magnetic elements 320 are located to the second side of the electrode connector axis 310 (e.g., to the left side as shown in FIG. 3) and to a second side of the electrode device line of symmetry 322 (e.g., below the electrode device line of symmetry 322 as shown in FIG. 3). In some embodiments, the arrangement of the magnetic elements 320 facilitates engagement of the wearable device connector portion 200 to the electrode device connector portion 300 as will be described hereinafter.

Figure 4A:
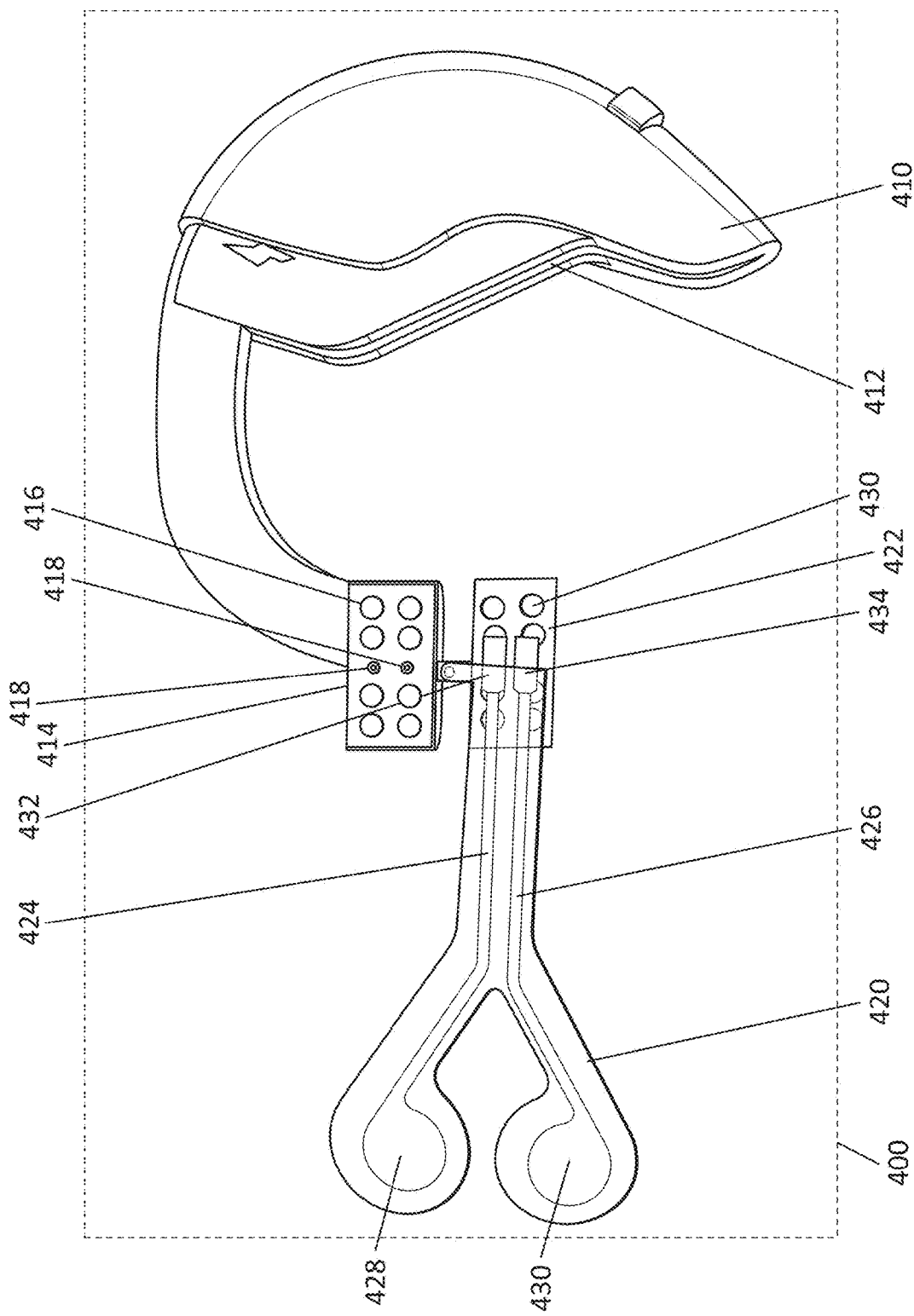
FIG. 4A shows an exemplary embodiment of a system including a wearable device and an electrode device, the system being shown in an unjoined position.

FIG. 4A shows an exemplary system 400 including a wearable device 410 and an electrode device 420. In the position shown in FIG. 4A, the wearable device 410 and the electrode device 420 have not yet been joined to one another. In the embodiment shown in FIG. 4A, the wearable device 410 includes a control portion 412 and a wearable device electrical connector portion 414. In some embodiments, the control portion 412 includes elements similar to those of the stimulator device 31 described above (e.g., a battery, a controller, a pulse generator, etc.). The wearable device electrical connector portion 414 is substantially similar to the wearable device connector portion 200 described above with reference to FIG. 2, and includes a plurality of magnets 416 (only one of which is specifically identified with a reference numeral in FIG. 4A for clarity) and two electrical connectors 418. The electrode device 420 includes an electrode device connector portion 422, electrical conductors 424 and 426, and electrodes 428 and 430. The electrode device connector portion 422 is substantially similar to the electrode device connector portion 300 described above with reference to FIG. 4A, and includes a plurality of magnetic elements 430 (only one of which is specifically identified with a reference numeral in FIG. 4A for clarity) and two electrical connectors 432.

Figure 4B:
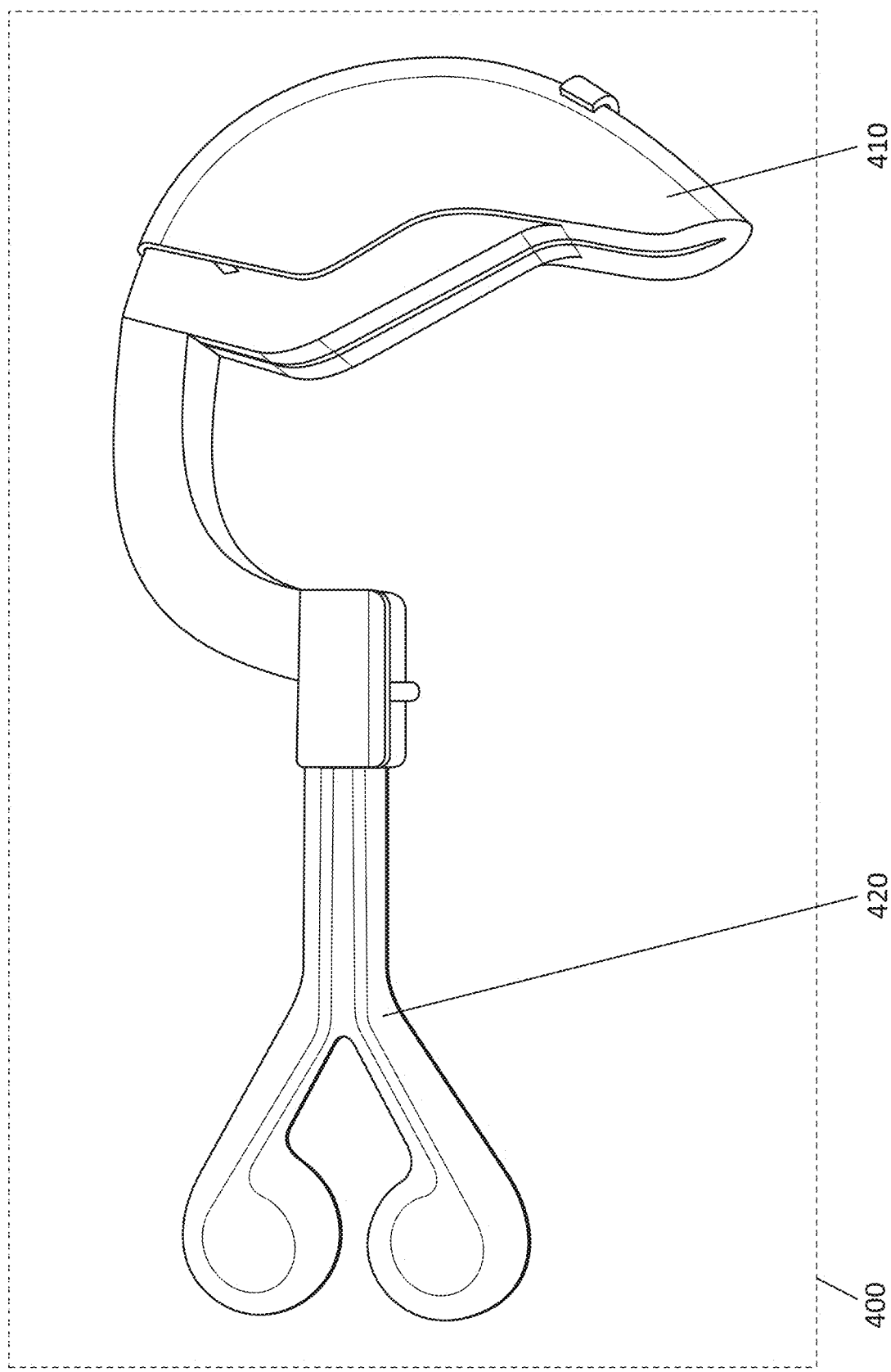
FIG. 4B shows the exemplary embodiment of a system shown in FIG. 4B, the system being shown in a joined position.

In some embodiments, the magnets 416 (e.g., which are substantially similar to the magnets 210 described above with reference to FIG. 2) and the magnetic elements 430 (e.g., which are substantially similar to the magnetic elements 320 described above with reference to FIG. 3) are configured (e.g., sized, shaped, and arranged) such that, when the electrode device connector portion 422 and the wearable device electrical connector portion 414 are brought together so as to bring the magnetic elements 430 into proximity to the magnets 416, a magnetic attractive force between the magnets 416 and the magnetic elements 430 holds the magnetic elements 430 in contact with the magnets 416. FIG. 4B shows the exemplary system 400 with the wearable device 410 and the electrode device 420 joined together by operation of the magnets 416 and the magnetic elements 430 in this manner. Further, in some embodiments, as a result of the specific positioning of the magnets 416 and the magnetic elements 430 (e.g., in the manner described above with reference to the magnets 210 shown in FIG. 2 and the magnetic elements shown in FIG. 3), the magnets 416 and the magnetic elements 430 act to position the electrical connectors 432 of the electrode device 420 in contact with respective ones of the electrical connectors 418 of the wearable device 410. In some embodiments, when the magnets 416 and the magnetic elements 430 are positioned in this manner, the electrode device line of symmetry (e.g., the electrode device line of symmetry 322 described above with reference to FIG. 3) and the wearable device line of symmetry (e.g., the wearable device line of symmetry 212 described above with reference to FIG. 2) align with one another to provide a single combined line of symmetry. In some embodiments, the magnets 416 and the magnetic elements 430, arranged as described above, cooperate to provide a magnetic attractive force that is evenly balanced to opposite sides of the combined line of symmetry. In some embodiments, such evenly balanced magnetic attractive force acts to maintain the electrical connectors 432 of the electrode device 420 in alignment with the electrical connectors 418 of the wearable device 410, thereby providing a continuous conductive path for electrical pulses generated by the wearable device 410 (e.g., in the manner described above with reference to FIG. 1) to be conveyed to the electrodes 428 and 430.

In some embodiments, the magnetic attractive force to a first side of the combined line of symmetry is equal to the magnetic attractive force to a second line of the combined line of symmetry. In some embodiments, the magnetic attractive force to a first side of the combined line of symmetry is sufficiently equivalent to the magnetic attractive force to the second line of the combined line of symmetry for the electrical connectors 418 and the electrical connectors 432 to be aligned as described above. In some embodiments, a sufficiently equivalent magnetic attractive force is within ±1%, or within ±2%, or within ±3%, or within ±4%, or within ±5%, or within ±6%, or within ±7%, or within ±8%, or within ±9%, or within ±10%, or within ±11%, or within ±12%, or within ±13%, or within ±14%, or within ±15%, or within ±16%, or within ±17%, or within ±18%, or within ±19%, or within ±20%.

FIG. 3 shows an exemplary embodiment of a magnetic connector including eight magnetic elements having a particular shape, size, and arrangement. In other embodiments, magnetic connectors have a different quantity of magnets (e.g., two magnets, three magnets, four magnets, five magnets, six magnets, seven magnets, nine magnets, ten magnets, etc.), a different shape (e.g., squares, rectangles, ovals, hollow circles, etc.), and/or arrangement. FIGS. 5A-5K show additional embodiments of arrangements of differently sized, shaped, and/or positioned magnetic elements that may be incorporated into an electrode device electrical connector similar to the electrode device connector portion 300 described above with reference to FIG. 3. In the embodiments shown in FIGS. 5A-5K, electrical connectors and conductors are omitted for clarity. In each of the embodiments shown in FIGS. 5A-5K, the magnetic elements are arranged in the manner described above with respect to FIG. 3, to thereby provide a suitable connection to a wearable device in the manner described above with reference to FIG. 4B.

Figure 5A:
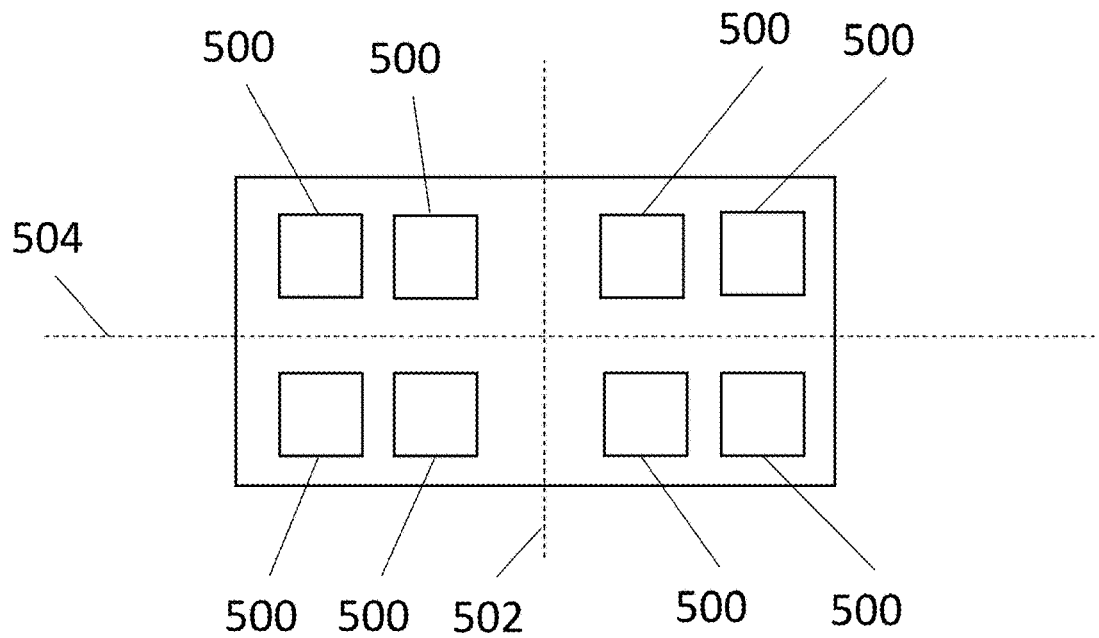
FIG. 5A shows an exemplary embodiment of an arrangement of magnetic elements.

FIG. 5A shows an embodiment including eight magnetic elements 500. In the embodiment shown in FIG. 5A, the magnetic elements 500 are rectangular (e.g., square). In the embodiment shown in FIG. 5A, the magnetic elements 500 are arranged such that four of the magnetic elements 500 are arranged to a first side of a connector axis 502 (e.g., as defined above), two of which are arranged to a first side of a device line of symmetry 504 (e.g., as defined above) and two of which are arranged to a second side of the device line of symmetry 504. In the embodiment shown in FIG. 5A, the magnetic elements 500 are further arranged such that four of the magnetic elements 500 are arranged to a second side of the connector axis 502, two of which are arranged to a first side of the device line of symmetry 504 and two of which are arranged to a second side of the device line of symmetry 504.

Figure 5B:
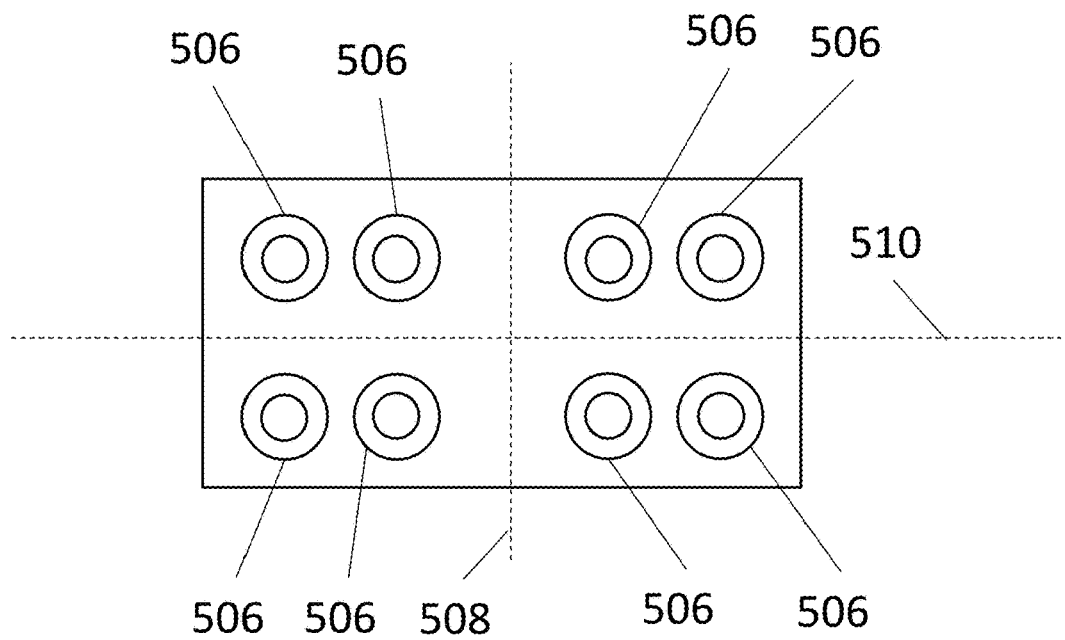
FIG. 5B shows an exemplary embodiment of an arrangement of magnetic elements.

FIG. 5B shows an embodiment including eight magnetic elements 506. In the embodiment shown in FIG. 5B, the magnetic elements 506 are annular. In the embodiment shown in FIG. 5B, the magnetic elements 506 are arranged such that four of the magnetic elements 506 are arranged to a first side of a connector axis 508 (e.g., as defined above), two of which are arranged to a first side of a device line of symmetry 510 (e.g., as defined above) and two of which are arranged to a second side of the device line of symmetry 510. In the embodiment shown in FIG. 5B, the magnetic elements 506 are further arranged such that four of the magnetic elements 506 are arranged to a second side of the connector axis 508, two of which are arranged to a first side of the device line of symmetry 510 and two of which are arranged to a second side of the device line of symmetry 510.

Figure 5C:
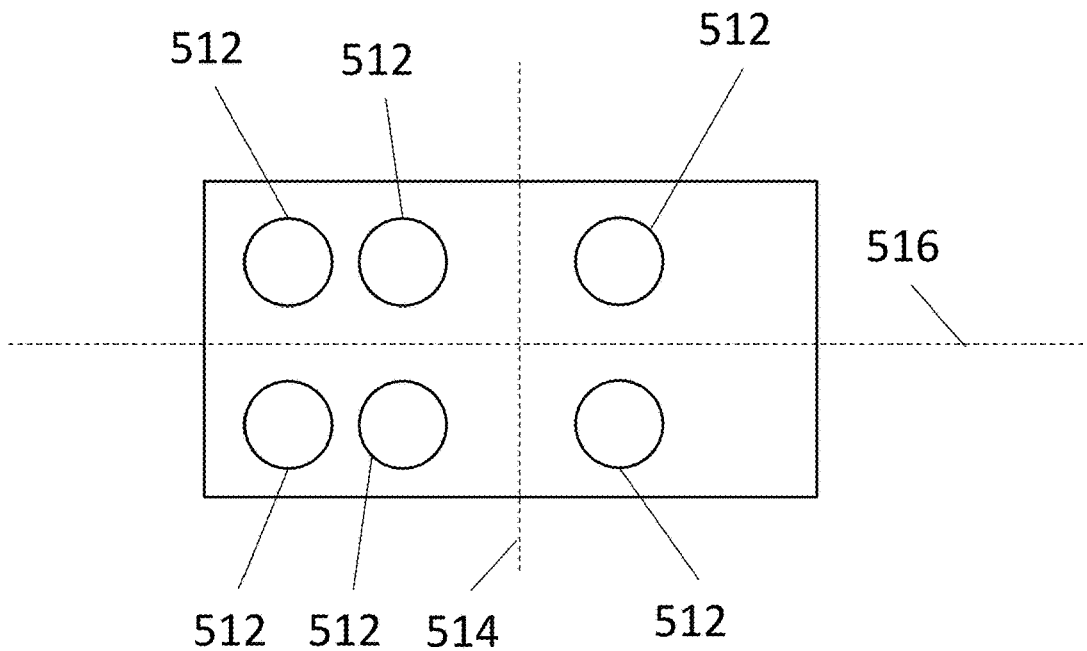
FIG. 5C shows an exemplary embodiment of an arrangement of magnetic elements.

FIG. 5C shows an embodiment including six magnetic elements 512. In the embodiment shown in FIG. 5C, the magnetic elements 512 are circular. In the embodiment shown in FIG. 5C, the magnetic elements 512 are arranged such that four of the magnetic elements 512 are arranged to a first side of a connector axis 514 (e.g., as defined above), two of which are arranged to a first side of a device line of symmetry 516 (e.g., as defined above) and two of which are arranged to a second side of the device line of symmetry 516. In the embodiment shown in FIG. 5C, the magnetic elements 512 are further arranged such that two of the magnetic elements 512 are arranged to a second side of the connector axis 514, one of which is arranged to a first side of the device line of symmetry 516 and one of which is arranged to a second side of the device line of symmetry 516.

Figure 5D:
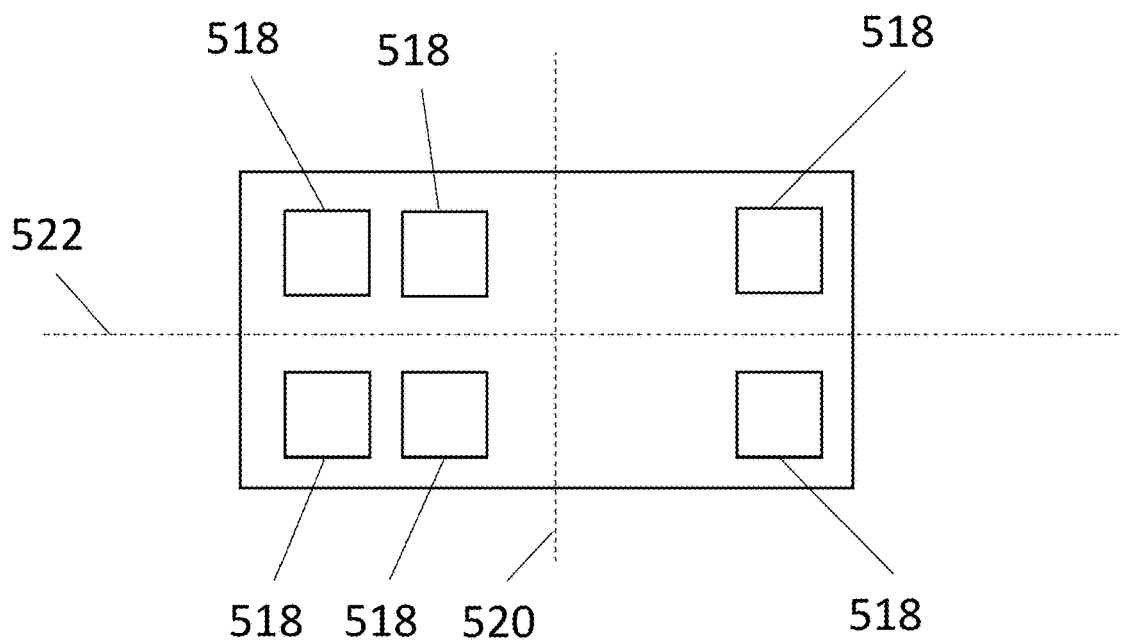
FIG. 5D shows an exemplary embodiment of an arrangement of magnetic elements.

FIG. 5D shows an embodiment including six magnetic elements 518. In the embodiment shown in FIG. 5D, the magnetic elements 518 are rectangular (e.g., square). In the embodiment shown in FIG. 5D, the magnetic elements 518 are arranged such that four of the magnetic elements 518 are arranged to a first side of a connector axis 520 (e.g., as defined above), two of which are arranged to a first side of a device line of symmetry 522 (e.g., as defined above) and two of which are arranged to a second side of the device line of symmetry 522. In the embodiment shown in FIG. 5D, the magnetic elements 518 are further arranged such that two of the magnetic elements 518 are arranged to a second side of the connector axis 520, one of which is arranged to a first side of the device line of symmetry 522 and one of which is arranged to a second side of the device line of symmetry 522.

Figure 5E:
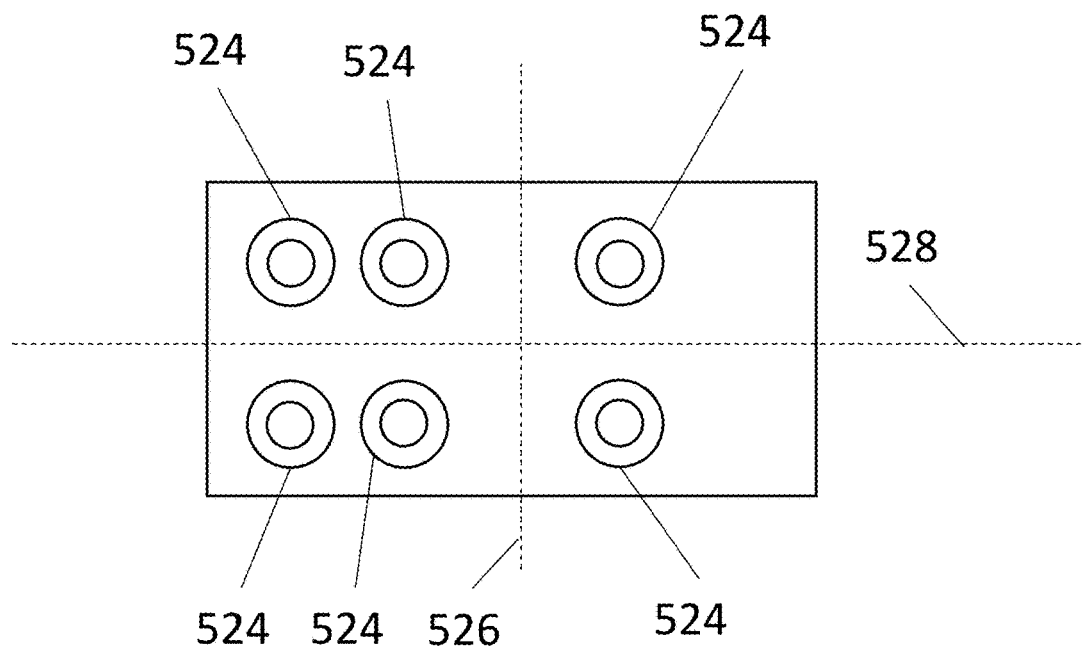
FIG. 5E shows an exemplary embodiment of an arrangement of magnetic elements.

FIG. 5E shows an embodiment including six magnetic elements 524. In the embodiment shown in FIG. 5E, the magnetic elements 524 are annular. In the embodiment shown in FIG. 5E, the magnetic elements 524 are arranged such that four of the magnetic elements 524 are arranged to a first side of a connector axis 526 (e.g., as defined above), two of which are arranged to a first side of a device line of symmetry 528 (e.g., as defined above) and two of which are arranged to a second side of the device line of symmetry 528. In the embodiment shown in FIG. 5E, the magnetic elements 524 are further arranged such that two of the magnetic elements 524 are arranged to a second side of the connector axis 526, one of which is arranged to a first side of the device line of symmetry 528 and one of which is arranged to a second side of the device line of symmetry 528.

Figure 5F:
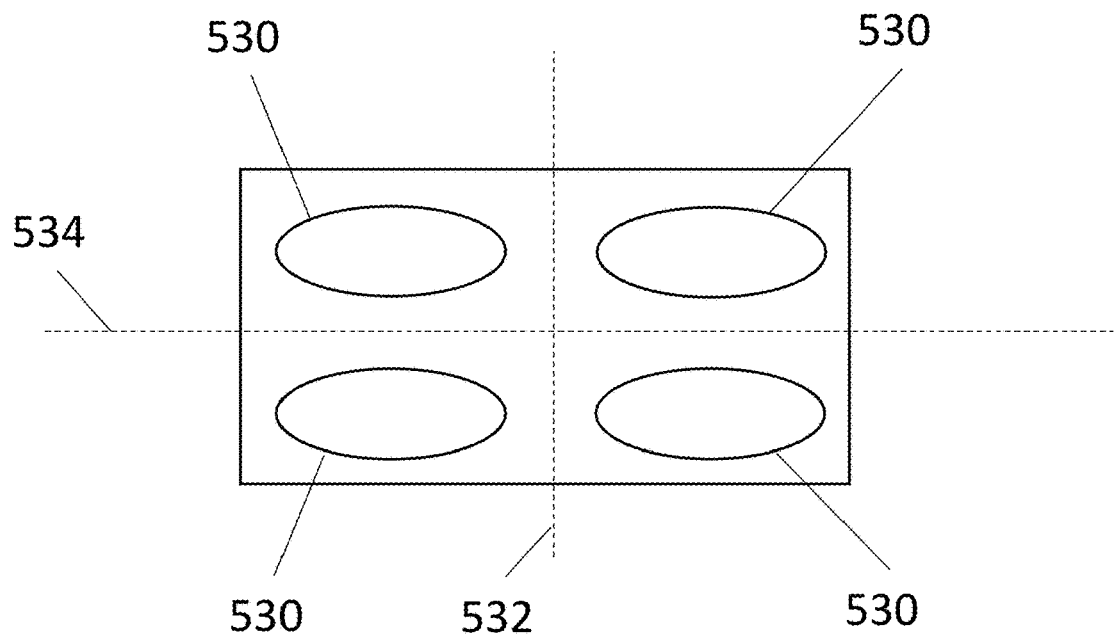
FIG. 5F shows an exemplary embodiment of an arrangement of magnetic elements.

FIG. 5F shows an embodiment including four magnetic elements 530. In the embodiment shown in FIG. 5F, the magnetic elements 530 are oval. In the embodiment shown in FIG. 5F, the magnetic elements 530 are arranged such that two of the magnetic elements 530 are arranged to a first side of a connector axis 532 (e.g., as defined above), one of which is arranged to a first side of a device line of symmetry 534 (e.g., as defined above) and one of which is arranged to a second side of the device line of symmetry 534. In the embodiment shown in FIG. 5F, the magnetic elements 530 are further arranged such that two of the magnetic elements 530 are arranged to a second side of the connector axis 532, one of which is arranged to a first side of the device line of symmetry 534 and one of which is arranged to a second side of the device line of symmetry 534.

Figure 5G:
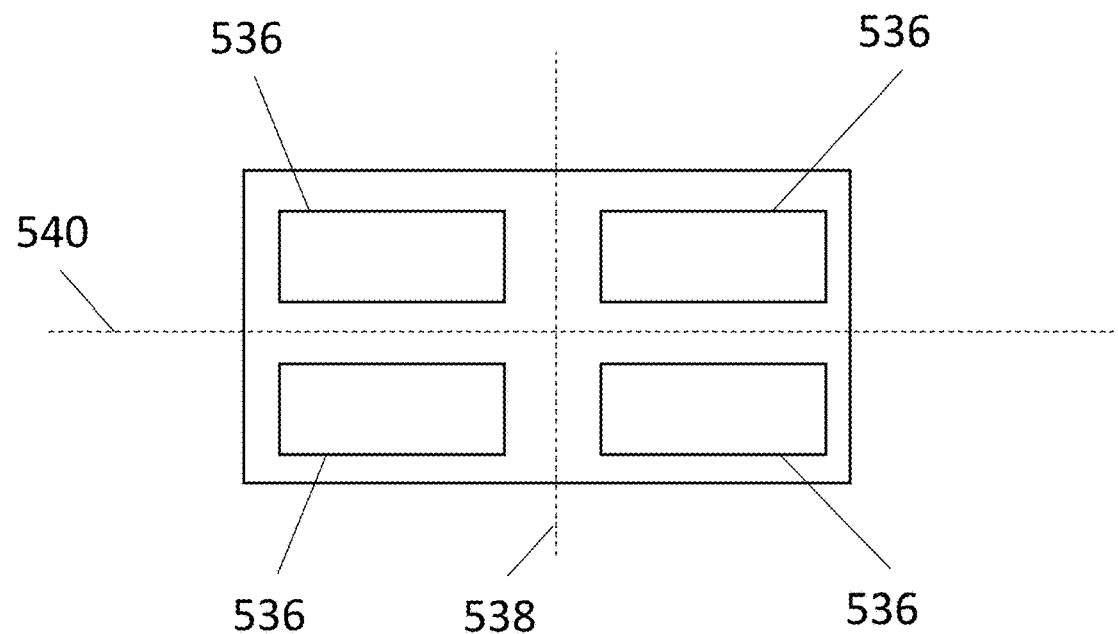
FIG. 5G shows an exemplary embodiment of an arrangement of magnetic elements.

FIG. 5G shows an embodiment including four magnetic elements 536. In the embodiment shown in FIG. 5G, the magnetic elements 536 are rectangular. In the embodiment shown in FIG. 5G, the magnetic elements 536 are arranged such that two of the magnetic elements 536 are arranged to a first side of a connector axis 538 (e.g., as defined above), one of which is arranged to a first side of a device line of symmetry 540 (e.g., as defined above) and one of which is arranged to a second side of the device line of symmetry 540. In the embodiment shown in FIG. 5G, the magnetic elements 536 are further arranged such that two of the magnetic elements 536 are arranged to a second side of the connector axis 538, one of which is arranged to a first side of the device line of symmetry 540 and one of which is arranged to a second side of the device line of symmetry 540.

Figure 5H:
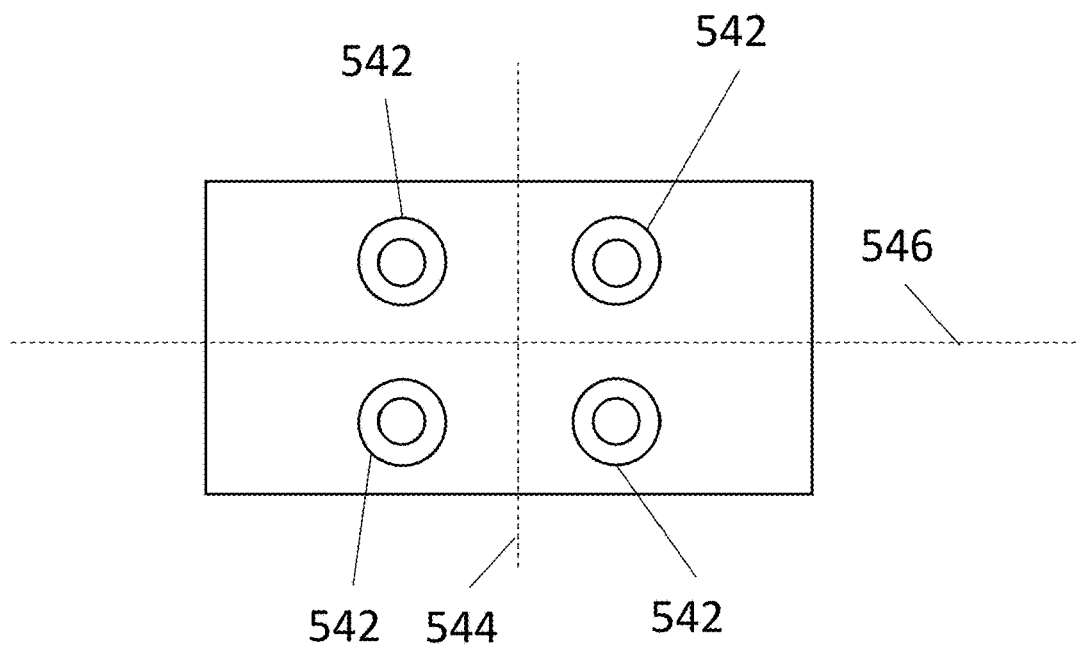
FIG. 5H shows an exemplary embodiment of an arrangement of magnetic elements.

FIG. 5H shows an embodiment including four magnetic elements 542. In the embodiment shown in FIG. 5H, the magnetic elements 542 are annular. In the embodiment shown in FIG. 5H, the magnetic elements 542 are arranged such that two of the magnetic elements 542 are arranged to a first side of a connector axis 544 (e.g., as defined above), one of which is arranged to a first side of a device line of symmetry 546 (e.g., as defined above) and one of which is arranged to a second side of the device line of symmetry 546. In the embodiment shown in FIG. 5H, the magnetic elements 542 are further arranged such that two of the magnetic elements 542 are arranged to a second side of the connector axis 544, one of which is arranged to a first side of the device line of symmetry 546 and one of which is arranged to a second side of the device line of symmetry 546.

Figure 5I:
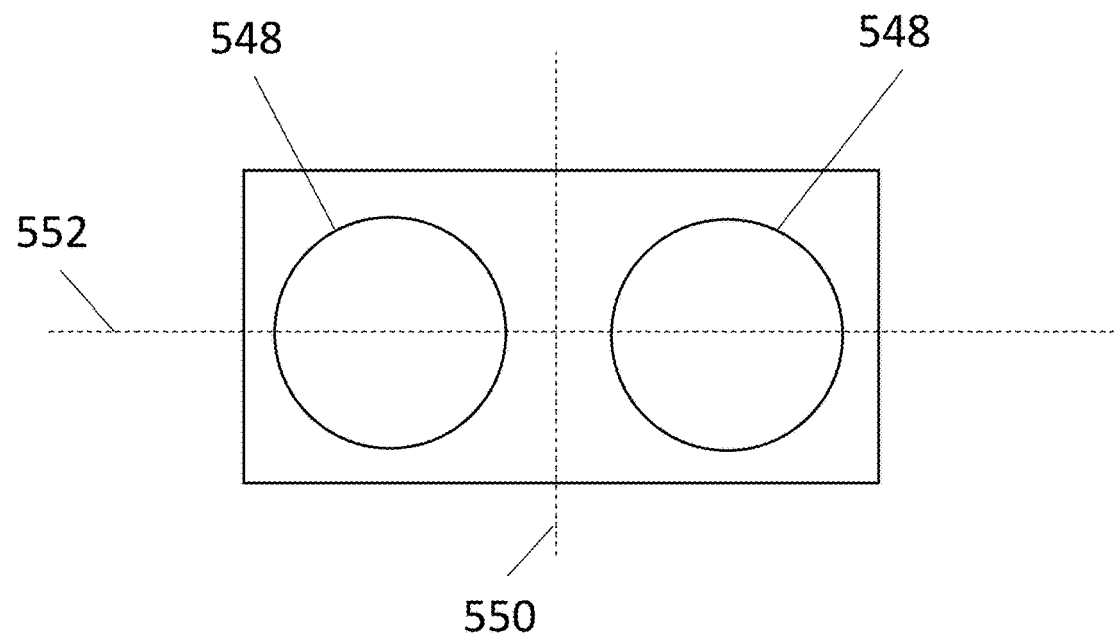
FIG. 5I shows an exemplary embodiment of an arrangement of magnetic elements.

FIG. 5I shows an embodiment including two magnetic elements 548. In the embodiment shown in FIG. 5I, the magnetic elements 548 are circular. In the embodiment shown in FIG. 5I, the magnetic elements 548 are arranged such that one of the magnetic elements 548 is arranged to a first side of a connector axis 550 (e.g., as defined above), a first portion of which is arranged to a first side of a device line of symmetry 552 (e.g., as defined above) and a second portion of which is arranged to a second side of the device line of symmetry 552. In the embodiment shown in FIG. 5I, the magnetic elements 548 are further arranged such that one of the magnetic elements 548 are arranged to a second side of the connector axis 550, a first portion of which is arranged to a first side of the device line of symmetry 552 and a second portion of which is arranged to a second side of the device line of symmetry 552.

Figure 5J:
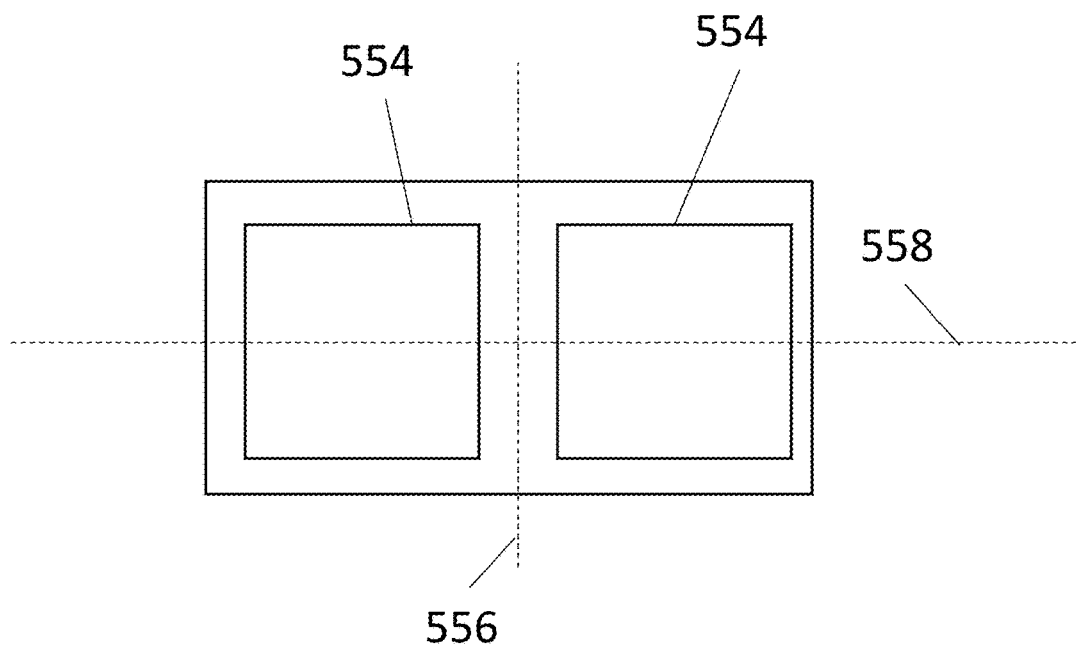
FIG. 5J shows an exemplary embodiment of an arrangement of magnetic elements.

FIG. 5J shows an embodiment including two magnetic elements 554. In the embodiment shown in FIG. 5J, the magnetic elements 554 are rectangular (e.g., square). In the embodiment shown in FIG. 5J, the magnetic elements 554 are arranged such that one of the magnetic elements 554 is arranged to a first side of a connector axis 556 (e.g., as defined above), a first portion of which is arranged to a first side of a device line of symmetry 558 (e.g., as defined above) and a second portion of which is arranged to a second side of the device line of symmetry 558. In the embodiment shown in FIG. 5J, the magnetic elements 554 are further arranged such that one of the magnetic elements 554 are arranged to a second side of the connector axis 556, a first portion of which is arranged to a first side of the device line of symmetry 558 and a second portion of which is arranged to a second side of the device line of symmetry 558.

Figure 5K:
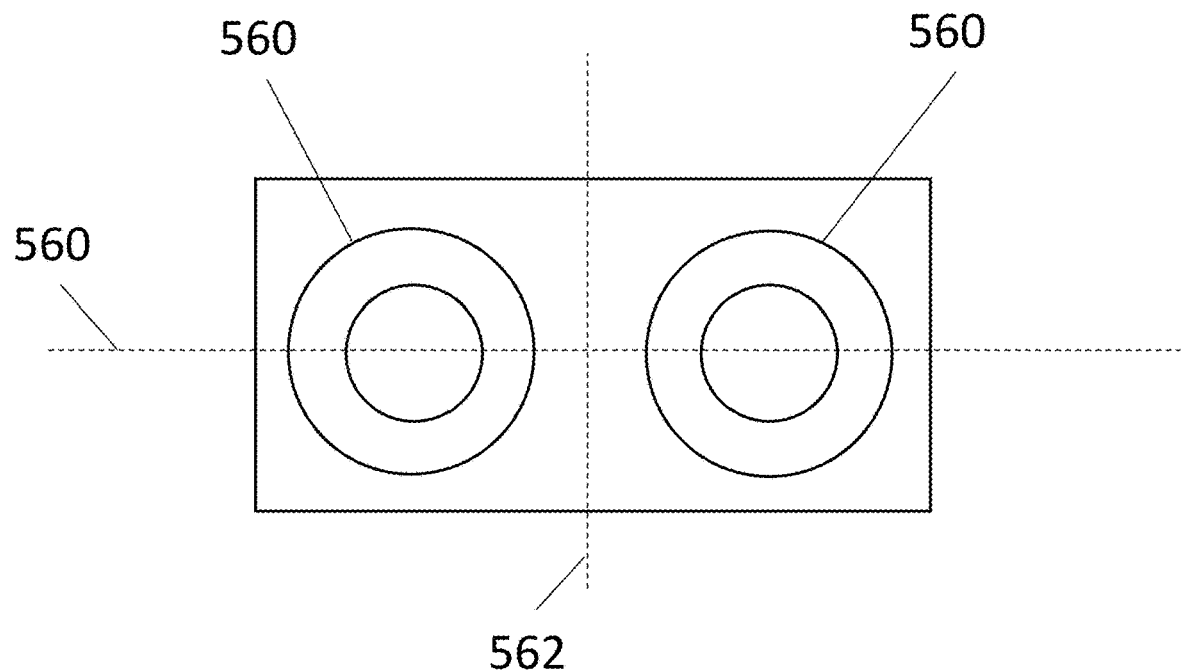
FIG. 5K shows an exemplary embodiment of an arrangement of magnetic elements.

FIG. 5K shows an embodiment including two magnetic elements 560. In the embodiment shown in FIG. 5K, the magnetic elements 560 are annular. In the embodiment shown in FIG. 5K, the magnetic elements 560 are arranged such that one of the magnetic elements 560 is arranged to a first side of a connector axis 562 (e.g., as defined above), a first portion of which is arranged to a first side of a device line of symmetry 564 (e.g., as defined above) and a second portion of which is arranged to a second side of the device line of symmetry 564. In the embodiment shown in FIG. 5K, the magnetic elements 560 are further arranged such that one of the magnetic elements 560 are arranged to a second side of the connector axis 562, a first portion of which is arranged to a first side of the device line of symmetry 564 and a second portion of which is arranged to a second side of the device line of symmetry 564.

Figure 5L:
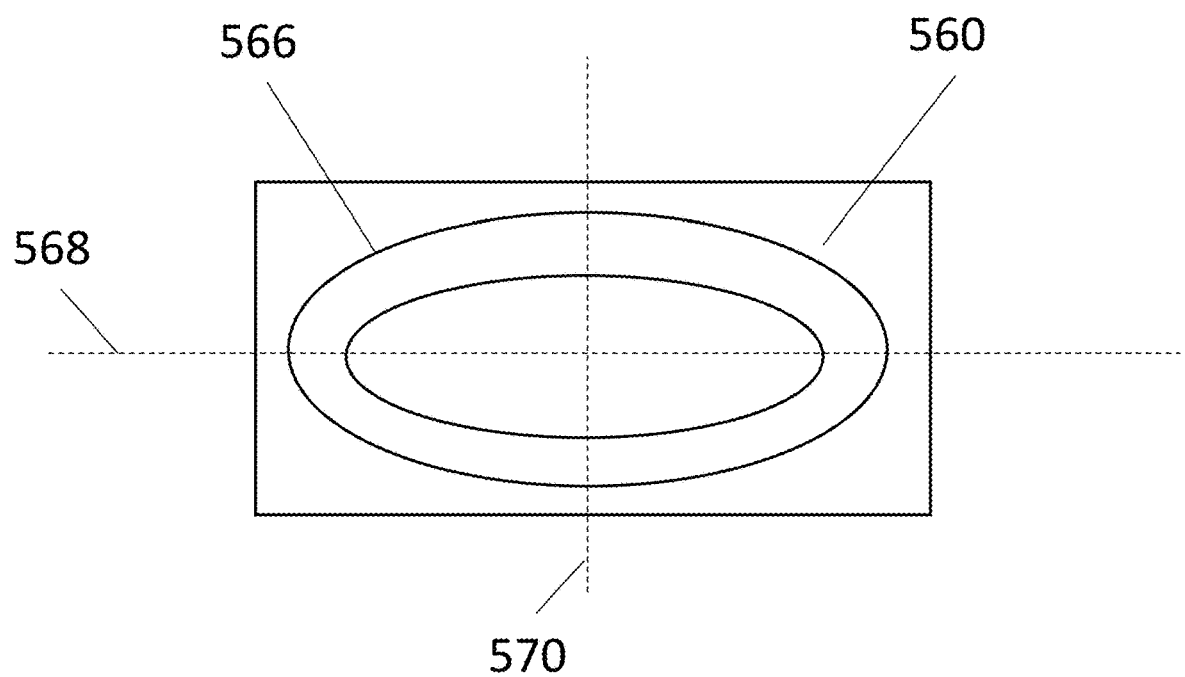
FIG. 5L shows an exemplary embodiment of an arrangement of a magnetic element.

In some embodiments, rather than including a plurality of magnetic elements, an electrode device electrical connector includes a single magnetic element that spans the electrode device electrical connector in a manner similar to the arrangements of a plurality of magnetic elements described herein. FIG. 5L shows an embodiment including such a magnetic element 566. In the embodiment shown in FIG. 5L, the magnetic element 566 is sized, shaped, and positioned such that a first portion of the magnetic element 566 is positioned to a first side of a connector axis 568 (e.g., as defined above), a first sub-portion of which is positioned to a first side of a device line of symmetry 570 (e.g., as defined above) and a second sub-portion of which is positioned to a second side of the device line of symmetry 570, and such that a second portion of the magnetic element 566 is positioned to a second side of the connector axis 568, a first sub-portion of which is positioned to a first side of the device line of symmetry 570 and a second sub-portion of which is positioned to a second side of the device line of symmetry 570. In some embodiments, an electrode device electrical connector including a magnetic element configured in this manner operates to provide electrical connection and alignment in the manner described above with reference to FIG. 4B. The magnetic element 566 is shaped as a hollow oval, but other embodiments having other shapes of a single magnetic element (e.g., a solid oval, a hollow rectangle, etc.) are also possible without departing from the principles described herein.

The specific arrangements of magnetic elements described herein are only exemplary, and other arrangements of magnetic elements in an electrode device connector portion are possible while being arranged in the manner described above with reference to FIG. 3 without departing from the principles embodied by the exemplary arrangements described herein.

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

What is claimed is:
1. A system, comprising:
a wearable device configured to artificially stimulate a facial nerve or muscle, the wearable device comprising:
  a pulse generator configured to generate a signal; and
  a wearable device connector portion, wherein the wearable device connector portion comprises:
    a first wearable device electrical connector,
    a second wearable device electrical connector,
      wherein the first wearable device electrical connector and the second wearable device electrical connector are electrically coupled to the pulse generator, and
      wherein the first wearable device electrical connector and the second wearable device electrical connector define a wearable device connector axis that extends through a center of the first wearable device electrical connector and a center of the second wearable device electrical connector, and
    at least four magnets,
      wherein a first at least one of the magnets is positioned to a first side of the wearable device connector axis,
      wherein a second at least one of the magnets is positioned to a second side of the wearable device connector axis that is opposite the first side of the wearable device connector axis, and
      wherein the at least four magnets define a wearable device line of symmetry; and
an electrode device, comprising:
  at least two electrodes,
    wherein the at least two electrodes are configured to be attachable to human body scalp at temporal skin of the human body scalp; and
  an electrode connector portion, wherein the electrode connector portion comprises:
    a first electrode electrical connector electrically coupled to a first one of the two electrodes,
    a second electrode electrical connector electrically coupled to a second one of the two electrodes,
      wherein the first electrode electrical connector and the second electrode electrical connector define an electrode connector axis that extends through a center of the first electrode electrical connector and a center of the second electrode electrical connector, and
    a plurality of magnetic elements,
      wherein the plurality of magnetic elements define an electrode device line of symmetry,
  wherein the at least four magnets and the plurality of magnetic elements are configured such that,
    when the electrode device is positioned adjacent to the wearable device such that the first wearable device electrical connector contacts the first electrode electrical connector, the second wearable device electrical connector contacts the second electrode electrical connector,
    a magnetic attractive force between the at least four magnets and the plurality of magnetic elements retains the wearable device connector portion of the wearable device and the electrode connector portion of the electrode device in proximity to one another,
    so as to result in the first wearable device electrical connector being maintained in contact with the first electrode electrical connector and the second wearable device electrical connector being maintained in contact with the second electrode electrical connector, thereby to allow the signal generated by the pulse generator to be conveyed to the two electrodes.

2. The system of claim 1, wherein the wearable device line of symmetry is perpendicular to the wearable device connector axis.

3. The system of claim 2, wherein the wearable device line of symmetry is equidistant from the center of the first wearable device electric connector and from the center of the second wearable device electric connector.

4. An electrode component, comprising:
wherein the electrode component is configured to magnetically connect to a wearable device configured to artificially stimulate a facial nerve or muscle, wherein the wearable device comprises:
a pulse generator configured to generate a signal; and
a wearable device connector portion, wherein the wearable device connector portion comprises:
a first wearable device electrical connector and a second wearable device electrical connector,
wherein the first wearable device electrical connector and the second wearable device electrical connector are electrically coupled to the pulse generator,
wherein the first wearable device electrical connector and the second wearable device electrical connector define a wearable device connector axis that extends through a center of the first wearable device electrical connector and a center of the second wearable device electrical connector, and
at least four magnets,
wherein a first at least one of the magnets is positioned to a first side of the wearable device connector axis,
wherein a second at least one of the magnets is positioned to a second side of the wearable device connector axis that is opposite the first side of the wearable device connector axis, and
wherein the at least four magnets define a wearable device line of symmetry;
wherein the electrode component comprises:
two electrodes,
wherein the electrodes are configured to be attachable to human body scalp at temporal skin of the human body scalp;
an electrode connector portion, wherein the electrode connector portion comprises:
a first electrode electrical connector electrically coupled to a first one of the two electrodes, and
a second electrode electrical connector electrically coupled to a second one of the two electrodes,
wherein the first electrode electrical connector and the second electrode electrical connector define an electrode connector axis that extends through a center of the first electrode electrical connector and a center of the second electrode electrical connector, and
a plurality of magnetic elements,
wherein the plurality of magnetic elements define an electrode device line of symmetry,
wherein the plurality of magnetic elements are configured such that, when the electrode device is positioned adjacent to the wearable device such that the first wearable device electrical connector contacts the first electrode electrical connector and the second device electrical connector contacts the second electrode electrical connector,
a magnetic attractive force between the at least four magnets and the plurality of magnetic elements retains the wearable device connector portion of the wearable device and the electrode connector portion of the electrode device in proximity to one another, so as to result in the first wearable device electrical connector being maintained in contact with the first electrode electrical connector and the second wearable device electrical connector being maintained in contact with the second electrode electrical connector, thereby to allow the signal generated by the pulse generator to be conveyed to the two electrodes.

5. The electrode component of claim 4, wherein the wearable device line of symmetry is perpendicular to the wearable device connector axis.

6. The electrode component of claim 5, wherein the wearable device line of symmetry is equidistant from the center of the first wearable device electric connector and from the center of the second wearable device electric connector.

7. The electrode component of claim 4, wherein the wearable device line of symmetry is equidistant from the center of the first electrode device electric connector and from the center of the second electrode device electric connector.

* * * * *